US006395772B1

(12) United States Patent
Upadhyay et al.

(10) Patent No.: US 6,395,772 B1
(45) Date of Patent: May 28, 2002

(54) METHOD FOR BLOCKING ENDOTHELIAL CELL-LEUKOCYTE ATTACHMENT BY INHIBITING EXPRESSION OF ADHESION MOLECULES ON THE VASCULAR ENDOTHELIUM FOR THERAPEUTIC APPLICATIONS

(75) Inventors: Shakti N. Upadhyay; Suman Dhawan, both of New Delhi (IN)

(73) Assignee: National Institute of Immunology, New Delhi (IN)

( * ) Notice: Subject to any disclaimer, the term of this patent is extended or adjusted under 35 U.S.C. 154(b) by 0 days.

(21) Appl. No.: 09/304,415

(22) Filed: May 3, 1999

Related U.S. Application Data

(63) Continuation-in-part of application No. 08/789,464, filed on Jan. 27, 1997, now Pat. No. 6,245,781.

(30) Foreign Application Priority Data

Feb. 14, 1996 (IN) .................................. 294/96

(51) Int. Cl.[7] ............................................ A61K 31/335
(52) U.S. Cl. ...................................................... 514/463
(58) Field of Search ........................................ 514/463

(56) References Cited

FOREIGN PATENT DOCUMENTS

JP          316051        12/1995

OTHER PUBLICATIONS

Hirai et al., "The effect of natural drugs on eotaxin production", Kanpo to Men'eki Arerugi, 12, pp. 38–47, 1998.*
The Merck Index, 10th Edition, Jun. 21, 1986, p. 1167, No. 1162.*
USP Dictionary of USAN and International Drug Names, p. 89, 1997.
Ghosh, A.K. et al., Ind. Journal of Medical Research 78, Sep. 1983, pp. 407–416.
Akhter, M.H., Ind. Journal of Medical Research 70, Aug. 1979, pp. 233–241.
Krey, A.K., Science, vol. 166, Nov. 1969, pp. 755–757.
Akhter, M.H., Indian Journal of Medical Research 65, 1, Jan. 1977, pp. 133–141.
Berlin, G., Agents–Actions, Apr. 1984, 14 (3–4), Abstract (401–4).
Berlin, G., Int. Arch. Allergy–Appl. Immunology, 1983, 71 (4), Abstract (332–9).
Bhakuni, D.S. et al., Ch. 2, Protoberberine Alkaloids for the Alkoloids vol. 28, 1986 Academic Press, pp. 95–99.
Sabir, M. et al., Indian Journal of Physiol. Pharacol. 22(1): pp. 9–23, 1978.
Abstract of JP 07316051 A, Feb. 12, 1996, Kiyosuke et al.
Fung–Leung et al., Transplantation, 60(4), 362–368, 1995.

* cited by examiner

*Primary Examiner*—Dwayne C. Jones
(74) *Attorney, Agent, or Firm*—Ladas & Parry

(57) ABSTRACT

A method for blocking the attachment of leukocytes to endothelial cells/lining of the blood vessels using a plant derived protoberberine alkaloid, berberine or its pharmaceutically acceptable salts. This prevents tissue damage to the surrounding tissue. The method also can be used to prevent and/or treat clinical manifestations that involve endothelial cell-leukocyte attachment, for example septic shock, arthritis, psoriasis, multiple sclerosis, allergic asthma, metastatic melanoma and graft rejection.

12 Claims, 5 Drawing Sheets

Figure 1:

METHOD FOR BLOCKING ENDOTHELIAL CELL-LEUKOCYTE ATTACHMENT BY INHIBITING EXPRESSION OF ADHESION MOLECULES ON THE VASCULAR ENDOTHELIUM FOR THERAPEUTIC APPLICATIONS

This application is a continuation-in-part of application 08/789,464 filed on Jan. 27, 1997now U.S. Pat. No. 6,245,781, the subject matter of which is incorporated by reference.

BACKGROUND

It is now being recognized that the pathological consequences of many immune system mediated diseases including endotoxin induced septic shock (1), arthritis (2), psoriasis (3), multiple sclerosis (4), allergic asthma (5), metastatic melanoma (6) and as well as graft rejection (7) is the result of endothelial cell leukocyte attachment mediated by the adhesion molecules (8). Adhesion molecules expressed on the surface of endothelial lining of the blood vessels allow leukocyte attachment and trafficking to the site of inflammation. Cytokines like TNF-α produced by macrophages in response to inflammatory stimuli, induce expression of adhesion molecules (ICAM/VCAM) on the endothelial cell surface. As a result, activated lymphocytes, monocytes, or neutrophils bearing the ligand for adhesion molecules adhere to the endothelial cells and cause damage to the vascular lining and the surrounding tissue due to release of free radicals and other lytic molecules. An agent that blocks the expression of adhesion molecules at the site of inflammation in response to any inflammatory stimuli may therefore prevent endothelial—leukocyte attachment and consequently may have preventive and/or therapeutic effects in clinical situation of septic shock, arthritis, psoriasis, multiple sclerosis, allergic asthma, metastatic melanoma and graft rejection. It has been discovered that berberine or its pharmaceutically acceptable salts block adhesion of molecules to endothelial cell surface.

Berberine may be isolated from *Berberis airistata*. *Berberis aristata* has been widely used in traditional Indian medicine for treatment of gastroenteritis, and skin and eye infections (Chopra et al., 1956; Nadkarni 1954). The chemistry and pharmacological effects of protoberberine alkaloids have been described in the scientific literature. Berberine has been reported to have direct anti-bacterial (Sado, 1947; Dutta and Panse, 1962), anti-amoebic (Subbaihah and Amin, 1967; Dutta and Iyer, 1968) and anti-leishmanial effects (Dasgupta and Dikshit, 1929; Steck, 1974; Ghosh et al., 1983, 1985) and cytotoxic effects against certain types of tumor cells (for review see Bhakuni and Jain 1986). Berberine has been shown to complex with DNA (Krey and Hahn 1969; Maitia and Chowdhuri, 1981) and is being used as a specific stain for mast cells because of its specificity of binding with herapin (Berlin and Enerback, 1983, 1984).

Japanese Patent 07-316051 published Dec. 5, 1995 (Kangegafuchi Chemical Co. Ltd.) discusses the use of berberine or its pharmacologically tolerable salt as an immunosuppressant specifically for autoimmune diseases such as rheumatism and for treatment of allergies and to prevent rejection of isografts. This reference discloses that berberine inhibits antibody production by B cells, suppresses humoral immunity and has no effect on propagation of T cells.

SUMMARY OF THE INVENTION

This invention describes a method for blocking the attachment of leukocytes to endothelial cells/lining of the blood vessels using a plant derived protoberberine alkaloid, berberine or its pharmaceutically acceptable salts.

An object of this invention is to inhibit the attachment of leukocytes to the endothelial cells/lining of the blood vessel due to inhibition of cytokine induced expression of adhesion molecules on the endothelial cells.

A further object of this invention relates to prevention of tissue damage by inhibiting the attachment of leukocytes to the endothelial cells/lining of the blood vessels.

Yet another object of this invention is a method for prevention and/or treatment of clinical manifestations that involve endothelial cell-leukocyte attachment, for example septic shock, arthritis, psoriasis, multiple sclerosis, allergic asthma, metastatic melanoma and graft rejection.

BIREF DESCRIPTION OF THE FIGURES

FIG. 1: Electron micrograph of kidney from a mouse challenged with endotoxin (LPS: 500 ug)) showing attachment of neutrophils with endothelial cells of glomerular capillary. Degenerative changes in surrounding tissue are shown.

Figure 2:
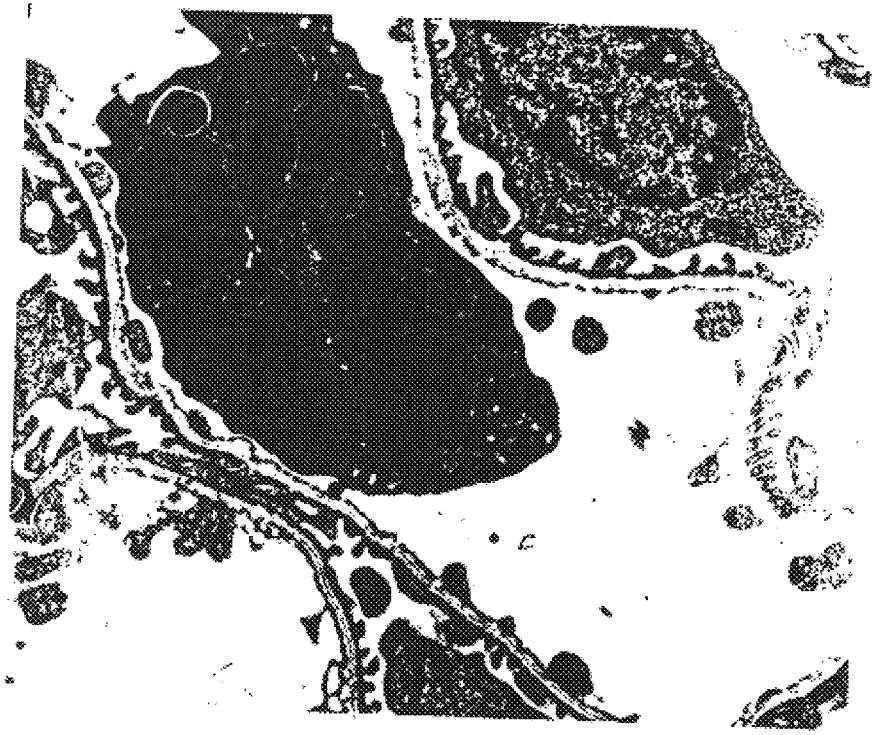

FIG. 2: Electron micrograph of kidney from a mouse treated with a dose of berberine of 10 mg/kg followed 24 hours later by endotoxin (LPS 500 ug). Neutrophils within glomerular capillary appear free without attachment to endothelial lining and the surrounding tissue appears normal.

Figure 3:
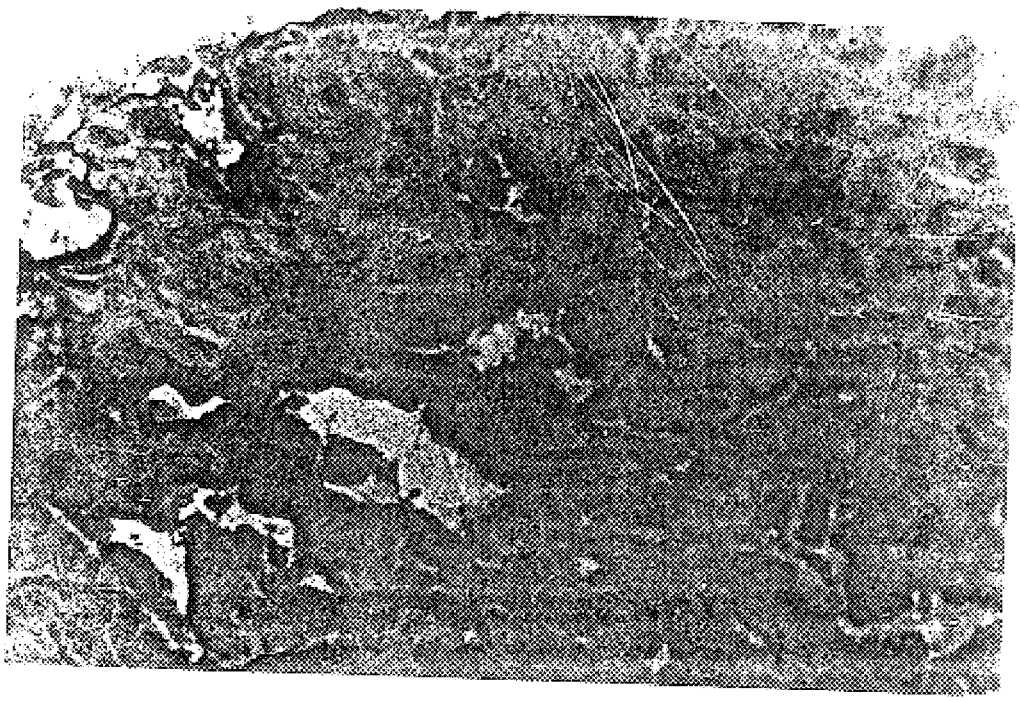

FIG. 3: Photomicrograph of liver from mice challenged with endotoxin (LPS 500 ug). Vascular endothelium shows very high level of expression of ICAM-1. (Immunocytochemical localization using anti-ICAM-1 antibody on frozen tissue).

Figure 4:
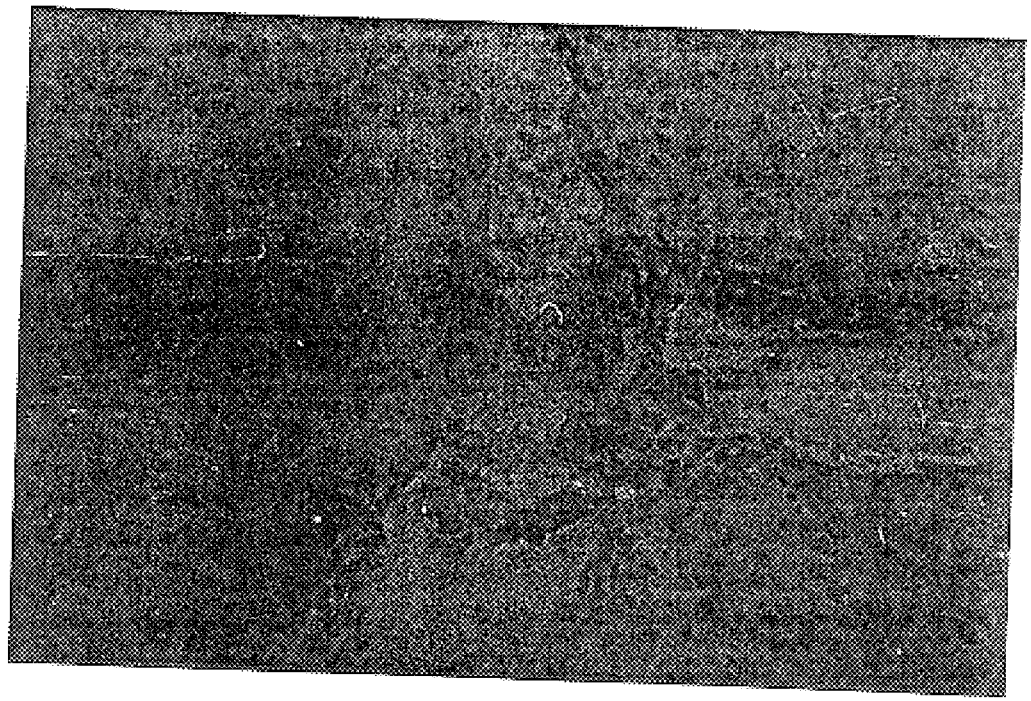

FIG. 4: Photomicrograph of liver from mice treated with berberine (10 ug/kg) followed 24 hours later by endotoxin (LPS 500 ug). Note lack of expression of ICAM-1 on vascular endothelium. (Immunocytochemical localization using anti-ICAM-1 antibody frozen tissue).

Figure 5:
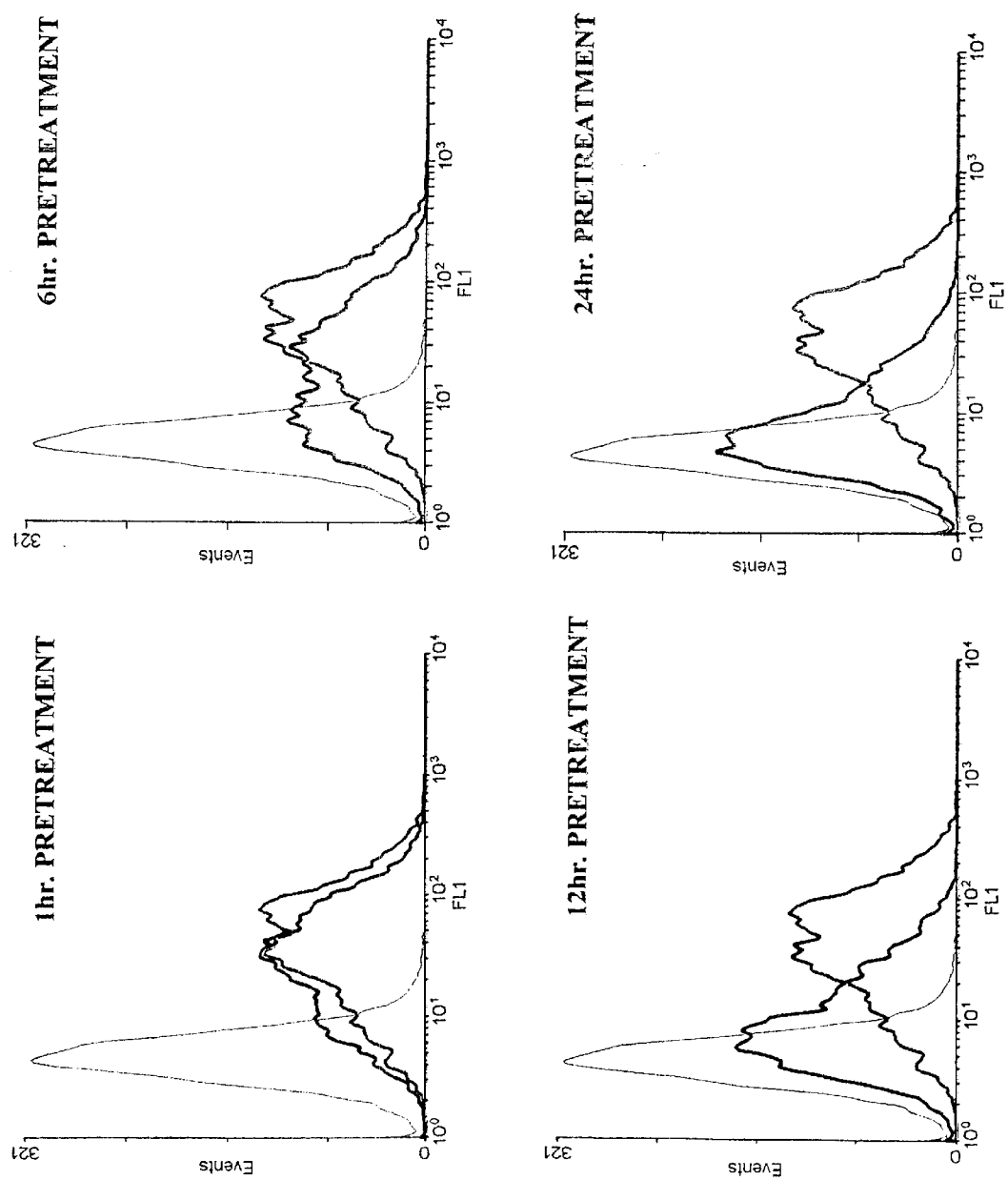

FIG. 5: Effect of berberine pretreatment on expression of TNF-α induced ICAM-1 expression on endothelial cell line (send. 1), in vitro. 24 hour pretreatment shows the maximum inhibition of ICAM-1 expression. (Flowcytometric analysis using anti-ICAM 1 antibody—FITC conjugate). The black line represents background level of ICAM expression, the red line represents induced level of ICAM following TNF stimulation and the green line represents TNF-α induced ICAM-1 expression after treatment for different duration.

Figure 6:
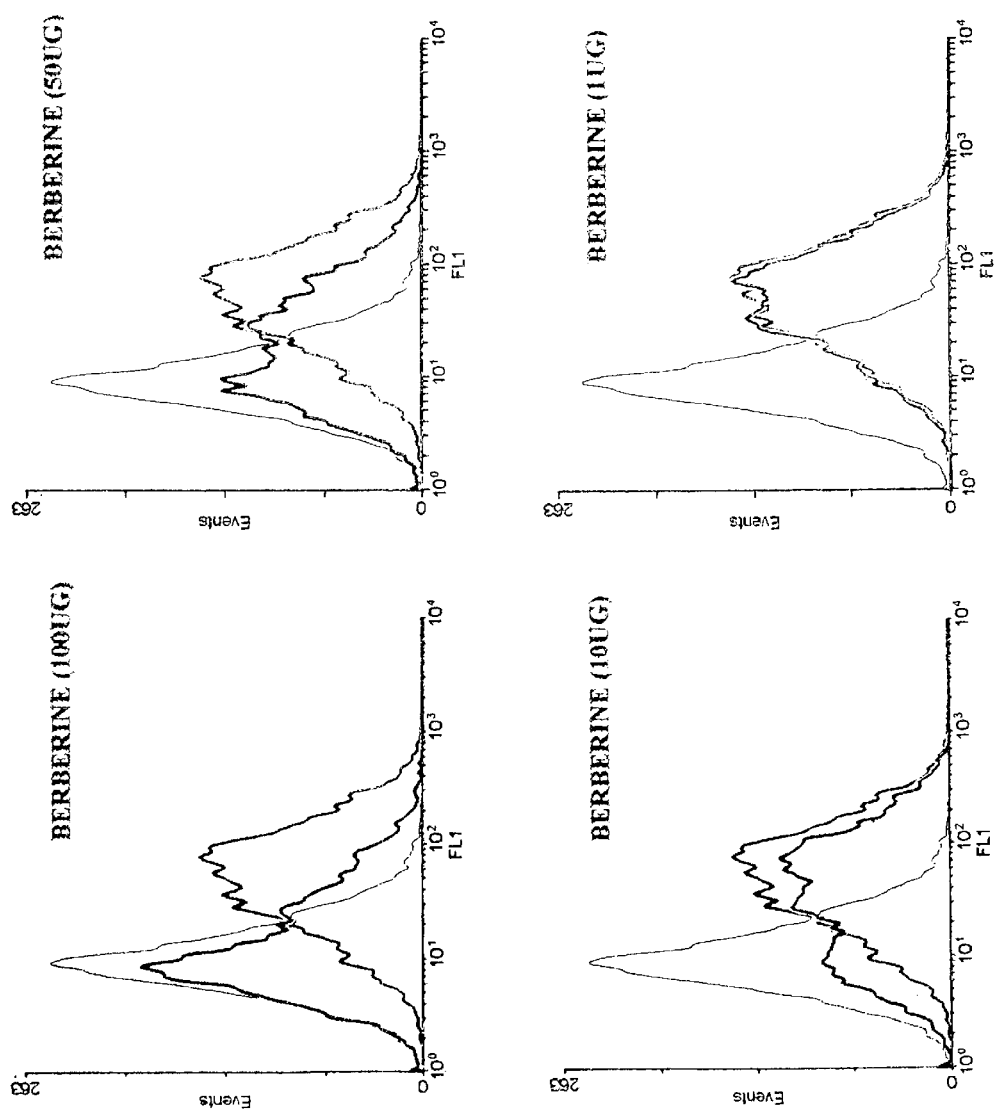

FIG. 6: Effect of berberine pretreatment (dose response) on expression of TNF-α induced ICAM-1 expression on endothelial cell line (send. 1), in vitro. Treatment with 100 ug/ml berberine shows the maximum inhibition of ICAM-1 expression. (Flowcytometric analysis using anti-ICAM 1 antibody—FITC conjugate). The black line represents background level of ICAM-1 expression, the red line represents induced level of ICAM following TNF stimulation and the green line represents the TNF-α induced ICAM induced ICAM expression after treatment with different doses of berberine.

Green line in both FIGS. 5 and 6 demonstrate the inhibitory effect of berberine on the TNF induced ICAM-1 expression, which is main contention of this invention. Shifting of this curve to the left indicates the lower amount of expression of ICAM-1.

Figure 7:
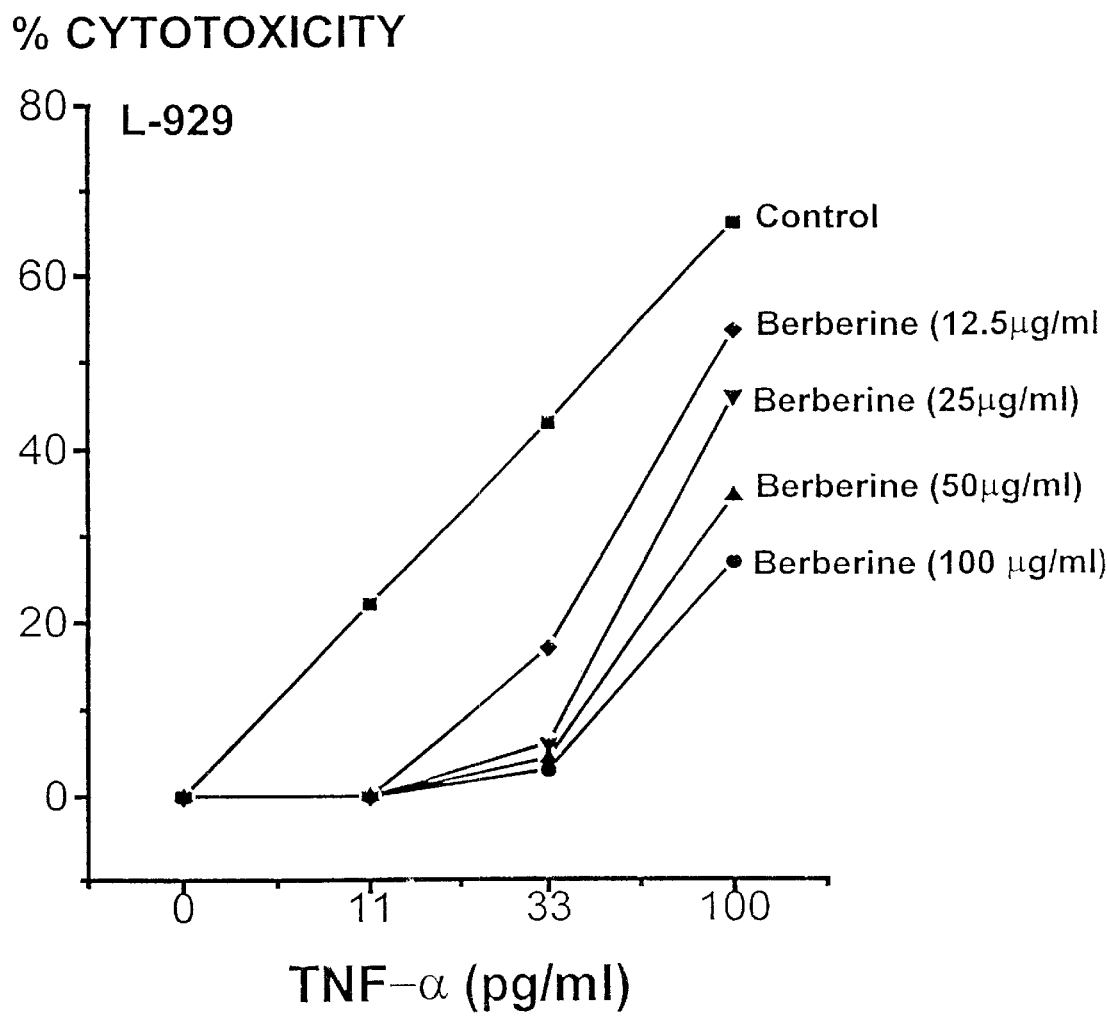

FIG. 7: Effect of berberine on TNF-α mediated cytotoxicity on TNF sensitive mouse fibroblast L-929 cell line. Berberine shows dose dependent inhibition of cytotoxic effect on TNF-α (viability measured by MTT assay).

DETAILED DESCRIPTION OF THE INVENTION

This invention is a method for blocking attachment of leukocytes to endothelial cells/lining of the blood vessels comprising administering to a mammal an amount of berberine or its pharmaceutically acceptable salts effective to block attachment of leukocytes to endothelial cells. Blocking the attachment of leukocytes to endothelial cells is by inhibition of cytokine induced expression of adhesion molecules on endothelial cells/lining of the blood vessels. Cytokines may be inflammatory cytokines such as TNF-α and IFN-γ. Adhesion molecules are molecules such as ICAM and VCAM.

A method for blocking attachment of leukocytes to endothelial cells comprises administering to a mammal an amount of berberine or its pharmaceutically acceptable salt effective to inhibit TNF-α induced expression of adhesion molecules such as ICAM and VCAM on the endothelial cells.

The method of this invention also involves blocking attachment of neutrophils, monocytes, macrophages or T cells to endothelial cells comprising administering to a mammal an amount of berberine or its pharmaceutically acceptable salts effective to block attachment of neutrophils, monocytes, macrophages or T cells to endothelial cells/lining of the blood vessels.

The blocking of the attachment of leukocytes inhibits TNF-α mediated pathogenic and cytotoxic effects including prevention and/or treatment of tissue damage to the surrounding tissue.

By blocking attachment of leukocytes to endothelial cells endotoxin induced septic shock, arthritis, psoriasis, multiple sclerosis, allergic asthma, metastatic melanoma or graft rejection may be prevented and/or treated.

Berberine is isolated from a medicinal plant, *Berberine aristata* and is also commercially available. Berberine and its pharmaceutically acceptable salts can also be produced synthetically (Kametani 1969 and Sainsburg 1969). Berberine or its pharmaceutically acceptable salts may be administered via any appropriate dosage routes, specifically, topically on skin or mucosal surfaces, orally, by injection, transdermally, intravenously, intraarterially, intraperitoneally, intrapleurally, subcutaneously, intramuscularly, sublingually, intranasally, by inhalation, intraepidermally, rectally or intravaginally. The preferred routes of administration are intravenously, intraarterially, orally or topically. Topical preparations include but are not limited to ointments, gels, salves, creams, lotions and sprays. Berberine and its pharmaceutically salts can also be administered in the forms of tablets, granules, powder, capsules, caplets and the like. Berberine salts are water soluble and can be administered in water. Berberine and its pharmaceutically acceptable salts can also be administered in other pharmaceutically acceptable carriers, diluents, solvents and excipients. Berberine or its salts may also be administered in a pharmaceutically acceptable liposomal preparation, lipid vesicle, microsphere, microcapsule, jelly, cream, spray, or aerosol.

The daily dose of berberine or its pharmaceutically acceptable salts is in the range of 1 to 20 mg/kg of body weight; preferably 5 to 10 of body weight. It is more preferred that the dosage be 10 mg/kg of body weight. The daily dose of berberine or its pharmaceutically acceptable salts can be administered as a single dose or in multiple doses.

Neutrophils, macrophages and T cells all use similar adhesion molecules (ICAM-1 and VCAM) on endothelial cells for their attachment since they all carry the ligand (LFA-1 or MAC-1) for these adhesion molecules. Therefore in the absence of these adhesion molecules on endothelial cells, all these cell types are expected to be affected.

This invention is demonstrated by the following examples, which illustrate the effect on neutrophils since these cells are involved in most situations of tissue damage. The examples, however, should not be construed as limiting the scope of the invention.

EXAMPLES

1. Berberine Treatment Inhibits Neutrophil Attachment to Endothelial Lining

BALB/C mice were treated with berberine (1, 5, 10 or 20 ug/kg body weight) intraperitoneally and challenged 24 hours later with lethal dose of endotoxin. Kidneys were removed after 3, 6 and 12 hours after endotoxin challenge and the tissue samples was fixed and processed for electron microscopy. Electron microscopic observations showed that endotoxin challenge induced widespread attachment of neutrophils to the capillary endothelium and tissue damage (FIG. 1) in control animals, whereas treatment with berberine remarkably inhibited the attachment of neutrophils to endothelial lining of the glomerular capillaries in spite of the presence of circulating neutrophils (FIG. 2); glomerular morphology was normal in groups treated with berberine with a dose of 10–20 mg/kg.

2. Berberine Treatment Inhibits Expression of ICAM-1 on Endothelial Lining

BALB/C mice were treated with berberine (1, 5, 10 or 20 ug/kg body weight) intraperitoneally and challenged 24 hours later with 500 ug of endotoxin (lipopolysaccharide: LPS); controls without berberine treatment were also given LPS challenge. Animals were sacrificed 6 hours after the LPS challenge and various organs (liver, kidney, lungs) were removed and immediately frozen in liquid nitrogen. Frozen section of these organs were subjected to immunocytochemical localization for ICAM 1 antibodies. In control animals, LPS induced expression of ICAM-1 on the vascular endothelium in control animals (FIG. 3), whereas berberine treatment inhibited expression of ICAM 1 on the endothelial lining of all organs including liver, kidney and lungs; ICAM-1 expression in liver is shown here as an example (FIG. 4).

3. Berberine Inhibits Expression of TNF-α Induced ICAM-1 on Endothelial Cells, in Vitro Effect of berberine for various duration ranging from 1, 6, 12 and 24 hours on the expression of ICAM-1 on the endothelial cell line (send. 1) in response to a combination of recombinant TNF-α and IFN-γ was analyzed using flow-cytometer after staining with FITC labeled anti-CD 54 (ICAM-1) antibody. Our results showed that berberine inhibited the expression of ICAM-1 on endothelial cells, as early as 6 hours of treatment. However maximum inhibition was seen at 24 hours of treatment at 100 μg/ml (FIG. 5). The inhibition of ICAM-1 expression was dose dependent (FIG. 6). These results confirm that berberine inhibits TNF-α induced expression of adhesion molecule, ICAM-1.

4. Berberine Inhibits TNF-α Mediated Cytotoxic Effect on TNF Sensitive Cells in Vitro Effect of Berberine on TNF-α mediated cytotoxicity was evaluated using TNF-sensitive L-929 fibroblast cell line. L-929 cells were plated at a concentration of $5 \times 10^4$ cells/well in a 96-well flat bottom plate in a volume of 100 μl. The cells were incubated at 37° C. for 16–18 hrs. Different concentrations of TNF-α, with and without different doses of berberine, were added to the cultures. The cells were then incubated for additional 15 hrs and cytotoxity was measured by MTT assay. TNF at a concentration of 100 pg/ml showed 66% cytotoxity (FIG. 7). Berberine showed a dose dependent protection against TNF mediated killing. At 100 µg/ml, Berberine reduced TNF mediated cytotoxity to 27%. These results demonstrates that berberine inhibits TNF induced signal transduction.

References:
1. Xu H, Ganzalo JA, Pierre Y. Williams IR, Kuppewr TS (1994) J. Exp. Med., 180:95
2. Seidel MF et al. (1997) J. Histo. Chem. Cytochem., 45: 1247–53
3. Lisby S, Ralfkiaer E, Rothlien R, Vejsgaard GL (1989) Br. J. Dermatol. 120: 479–484
4. Sobel RA, Mitchell ME, Fondren G (1990) Am. J. Pathol., 136: 1309–1316
5. Wegner CD, Gundel RH, Reilly P, Haynes N, Letts LG, Rothlien R (1990) Science, 247: 456–459
6. Johnson JP, Stade BG, Holzmann B, Schwable W, Reitlhmuller G (1989) Proc. Nat. Acad. Sci., USA, 86: 641–644
7. Adams DH, Hybscher SG, Shaw J, Rothlirn R, Neuberger I (1989) Lancet 2: 1122–1125
8. Bevilacqua, MP, Nelson R, Mannori G, Cecconi Oliviero, Annv. Rev. Med. 1994, 45: 361–78.

What is claimed is:

1. A method for blocking attachment of leukocytes to endothelial cells comprising administering to a mammal an amount of berberine or its pharmaceutically acceptable salt effective to block attachment of leukocytes to endothelial cells.

2. The method according to claim 1, wherein the use of berberine or its salt in blocking the attachment of leukocytes to endothelial cells is by inhibition of cytokine induced expression of adhesion molecules on endothelial cells/lining of a blood vessel.

3. The method according to claim 2, wherein berberine or its salt inhibits leukocyte-endothelial attachment induced by cytokines.

4. The method according to claim 3, wherein the cytokine is TNF-α.

5. The method according to claim 3, wherein the cytokine is IFN-γ.

6. The method according to claim 4, wherein berberine or its salts inhibits TNF-α mediated pathogenic and cytotoxic effects.

7. The method according to claim 2, wherein the adhesion molecule is ICAM.

8. The method according to claim 2, wherein the adhesion molecule is VCAM.

9. The method according to claim 1, wherein berberine or its salt is administered topically, orally, by injection, transdermally, intravenously, intraarterially, intraperitoneally, intrapleurally, subcutaneoulsy, intramuscularly, sublingually, intranasally, by inhalation, intraepidermally, rectally or intravaginally.

10. The method according to claim 1, wherein berberine or its salt is administered in a pharmaceutically acceptable carrier, diluent, solvent or excipient.

11. The method according to claim 1, wherein berberine or its salts is administered in a liposomal preparation, lipid vesicle, microsphere, microcapsule, jelly, cream, spray, or aerosol.

12. A method for blocking attachment of leukocytes to endothelial cells comprising administering to a mammal an amount of berberine or its pharmaceutically acceptable salt effective to inhibit TNF-α induced expression of ICAM-1 on the endothelial cells.

* * * * *